United States Patent [19]

Merger et al.

[11] Patent Number: 4,695,645

[45] Date of Patent: Sep. 22, 1987

[54] PROCESS FOR THE PREPARATION OF N,O-SUBSTITUTED MONO-AND/OR POLYURETHANES

[75] Inventors: Franz Merger, Frankenthal; Friedrich Towae, Ludwigshafen, both of Fed. Rep. of Germany

[73] Assignee: BASF Aktiengesellschaft, Ludwigshafen, Fed. Rep. of Germany

[21] Appl. No.: 632,840

[22] Filed: Jul. 20, 1984

[30] Foreign Application Priority Data

Aug. 2, 1983 [DE] Fed. Rep. of Germany ....... 3327824

[51] Int. Cl.$^4$ .......................................... C07C 125/065
[52] U.S. Cl. ......................................... 560/24; 560/25; 560/26; 560/29; 560/32; 560/33; 560/157; 560/158; 560/160; 560/162; 560/166
[58] Field of Search .................... 560/24, 25, 26, 29, 560/32, 33, 157, 158, 160, 162, 166

[56] References Cited

U.S. PATENT DOCUMENTS 3,392,184  7/1968  Ulrich et al. .......................... 560/24
4,388,238  6/1983  Heitkämper et al. ................ 560/24

Primary Examiner—John Kight
Assistant Examiner—M. L. Moore
Attorney, Agent, or Firm—Norbert M. Lisicki

[57] ABSTRACT

The invention describes a process for the preparation of N,o-substituted mono- and/or polyurethanes of formula $$R^1[-NHCOOR^2]_m,$$

in which
$R^1$ is an aliphatic, cycloaliphatic, aromatic, araliphatic, or heterocyclic radical, which may be substituted,
$R^2$ is an aliphatic, cycloaliphatic, or araliphatic radical which may be substituted with alkoxy or polyoxyalkylene groups, and
is a whole number from 1 to 5, through the reaction of N-substituted allophanates and/or polyallophanates with alcohols $R^2OH$ in the presence or absence of catalysts at temperatures of at least 160° C., preferably from 165° to 250° C.

9 Claims, No Drawings

PROCESS FOR THE PREPARATION OF N,O-SUBSTITUTED MONO-AND/OR POLYURETHANES

BACKGROUND OF THE INVENTION

1. Field of the Invention

The invention relates to a process for the preparation of N,o-substituted mono- and/or polyurethanes of formula $$R^1[-NHCOOR^2]_n,$$

in which
R$^1$ is an aliphatic, cycloaliphatic, aromatic, araliphatic, or heterocyclic radical, which may be substituted,
R$^2$ is an aliphatic, cycloaliphatic, or araliphatic radical which may be substituted with alkoxy or polyoxyalkylene groups, and
n is a whole number from 1 to 5.

More particularly, the invention relates to a process for the preparation of N,o-substituted mono- and/or polyurethanes through the reaction of N-substituted allophanates and/or polyallophanates with alcohols R$^2$OH in the presence or absence of catalysts at temperatures of at least 160° C., preferably from 165° to 250° C.

2. Prior Art

Industrially, urethanes are generally produced by the reaction of isocyanates with alcohols or of chloroformates with amines, whereby both the isocyanates and the chloroformates are obtained through the phosgenation of the corresponding amines and cleaving off hydrogen chloride or by the phosgenation of the alcohols (*Methoden de organischen Chemie,* Houben-Weyl, vol. 8, pp. 137, 120, and 101, Stuttgart: Georg Thieme Verlag, 1952). These processes are very expensive from a commercial standpoint; in addition, the use of phosgene results in significant disadvantages relating to the necessary safety and environmental measures.

Recently, a series of processes for producing urethanes has been described in which carboxylic acid derivatives are reacted with primary amines in the presence of alcohols.

In European Patent Application No. 18 581 (Canadian Pat. No. 1,121,373), aryl-mono- and/or -polyurethanes are prepared by reacting o-alkylcarbamates with primary aromatic mono- and/or polyamines in the presence of alcohols and, in some cases, urea. In German Application No. 31 22 013, N,N'-diarylureas are cited as the carboxylic acid derivatives, and in German Application No. 30 35 354, dialkylcarbonates are cited as the carboxylic acid derivatives.

In addition, *Methoden der organischen Chemie,* Houben-Weyl, vol. 8, mentions the alcoholysis of unsubstituted allophanates of formula H$_2$N—CO—N-H—CO—OR to form N-unsubstituted carbamates (p. 206). No industrial teachings are given on the preparation of N-substituted urethanes.

German Application No. 31 08 067 describes a process for the preparation of N,o-disubstituted urethanes by reacting primary amines and alcohols with allophanates or mixtures of allophanates, urea, and/or carbamates, said mixtures possessing allophanates, at temperature of from 130° to 350° C. The presence of amines is absolutely necessary for the reaction to take place. This is also demonstrated by the examples.

DESCRIPTION OF THE PREFERRED EMBODIMENT

It was now unexpectedly discovered that N,o-substituted mono- and/or polyurethanes can be prepared in a simple manner and with good yield when N-substituted allophanates and/or polyallophanates are alcoholized.

Hence, the subject of the invention is a process for the preparation of N,o-substituted mono- and/or polyurethanes of formula $$R^1[-NHCOOR^2]_n,$$

in which
R$^1$ is an aliphatic, cycloaliphatic, aromatic, araliphatic, or heterocyclic radical, which may be substituted,
R$^2$ is an aliphatic, cycloaliphatic, or araliphatic radical which may be substituted with alkoxy or polyoxyalkylene groups, which may be the same or different if n is greater than 1, and
n is a whole number from 1 to 5,
wherein N-substituted allophanates acid and/or polyallophanate is reacted with alcohols R$^2$OH in the absence or, preferably, in the presence of catalysts at temperatures of at least 160° C.

The process of the invention advantageously permits the N-substituted allophanates and/or polyallophanates obtained as by-products in the thermal cleavage of urethanes to isocyanates to be converted into urethanes, and thus made accessible for the preparation of isocyanate.

Allophanates and/or polyallophanates suitable for use as starting components, which may be exemplified for monovalent R$_1$ radicals by the formula $$R^1-NH[-CONR^1-]_x-COOR^3,$$

in which R$^1$ has the meaning described above, R$^3$ is an aliphatic, cycloaliphatic, aromatic, araliphatic, or heterocyclic radical, which may be substituted, and which preferably corresponds to the radical R$^2$, and x is a whole number of at least 1, preferably from 1 to 4, can be prepared according to known methods. Typical methods are the acylization of alcohols with substituted urea chloride or substituted allophanic acid chloride, or the direct introduction of the carboxylic ester group to the substituted urea with a carboxylic acid dialkyl ester or alkyl chloroformate. The substituted allophanates and/or polyallophanates are preferably prepared through the reaction of urethanes or alcohols with one or more moles of isocyanate or they are accumulated as by-products, corresponding to this reaction, especially in the thermal cleavage of urethanes to form isocyanates.

Suitable R$^2$OH alcohols for the process of the invention are linear or branched alkanols having from 1 to 18, preferably 1 to 10, and more preferably 3 to 6 carbon atoms, linear or branched alkanols substituted with alkoxy groups having from 1 to 4 carbon atoms or polyoxyalkylene groups, said alkanols containing from 2 to 24 carbon atoms, preferably from 4 to 8 carbon atoms, cycloaliphatic alcohols having from 4 to 12 carbon atoms, preferably from 6 to 8 carbon atoms, and/or araliphatic alcohols having from 7 to 15 carbon atoms, preferably from 7 to 10 carbon atoms. Specific examples of such alcohols are: methanol, ethanol, propanol, isopropanol, butanol, isobutanol, pentanol, isopentanol, hexanol, isohexanol, heptanol, isoheptanol, octanol, isooctanol, nonanol, isononanol, decanol, isodecanol, dodecanol, 2-ethylhexanol, 2-ethylbutanol, hexadecanol, octadecanol, 2-methoxyethanol, 2-ethoxyethanol, 2-propoxyethanol, 2-butoxyethanol, 2-(2-methoxyethoxy)ethanol, 2-(2-butoxyethoxy)ethanol, cyclopentanol, cyclohexanol, methylcyclohexanols, cyclohexamethanol, 3,3,5-trimethylcyclohexanol, 4-tert.-butylcyclohexanol, 2-hydroxydecalin, Borneol, Isoborneol, 2-hydroxyethoxybenzene, benzyl alcohol, 2-phenylethanol, 2-(methoxyphenoxy)ethanols, 1-phenylethanol, 3-phenyl-1-propanol, 4-methoxybenzyl alcohol.

Especially desirable and, therefore, preferred alcohols are: methanol, ethanol, n-propanol, isopropanol, n-butanol, isobutanol, n-pentanol, hexanol, heptanol, octanol, nonanol, decanol, ethylhexanol, cyclopentanol, benzyl alcohol, cyclohexanol, and 2-phenylethanol. These alcohols can be used separately or in the form of mixtures.

Since the alcohols are preferably used in a molar excess in the process of the invention, it is generally not necessary to add solvents. However, when special alcohols are used, it may be desirable to mix such alcohols with solvents or solvent mixtures which are inert at the reaction conditions, nonpolar, or preferably polar, and which have boiling points from 50° to 350° C. Typical examples of such solvents are: n-nonane, n-decane, n-dodecane, n-butylcyclohexane, n-hexylcyclohexane, decahydronaphthalene, isopropylbenzene, 1,3-diethylbenzene, n-butylbenzene, chlorobenzene, 4-chlorotoluene, 1,2-dichlorobenzene, 2,4-dichlorotoluene, 1,2,4-trichlorobenzene, 2-chloro-4-isopropyl-1-methylbenzene, anisol, cyclohexylethyl ether, diethylene glycol dimethyl ether, benzyl methyl ether, 4-methoxytoluene, parachloroanisol, di-n-hexyl ether, N,N-dimethylformamide, N,N-diethylformamide, N-methylformamide, dimethylacetamide, N-methylpyrrolidone, caprolactam, tetraline, sulfolane, hexamethylphosphoric acid triamide, dimethyl sulfoxide, ethylene glycol monomethyl ether acetate, Di-n-propyl carbonate, cyclohexyl acetate, diisobutyl carbonate, 2-ethylpyridine, N,N-dimethyl-2-methylaniline, N,N-dimethylaniline, N-methyl-N-ethylaniline, N,N-dimethyl-2-chloroaniline, N,N-diethylaniline, quinoline, nitrobenzene, 2-nitrotoluene, 2,4-dimethyl-1-nitrobenzene, acetonitrile, N-capronitrile, benzonitrile, tolunitrile, and phenylacetonitrile.

The alcoholysis of the allophanates and/or polyallophanates can be performed in the absence of catalysts. In order to increase the rate of reaction, and, hence, volume/time yield, it has been found to be advantageous to perform the reaction in the presence of one or more catalysts. Suitable catalysts are inorganic and organic compounds containing one or more, preferably one, cation of the metals in groups IA, IB, IIA, IIB, IIIA, IIIB, IVA, IVB, VA, VB, VIB, VIIB and VIIIB of the periodic system, defined in accordance with the *Handbook of Chemistry and Physics,* 14th Edition, (Cleveland, Ohio: Chemical Rubber Publishing Co., 2310 Superior Ave., N.E.), for example, halogenides such as chlorides and bromides, sulfates, phosphates, nitrates, borates, alcoholates, phenolates, sulfates, oxides, oxide hydrates, hydroxides, carboxylates, chelates, carbonates, and thio- or dithiocarbamates. Typical cations are those of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt, and nickel. Preferably, the cations of lithium, calcium, aluminum, tin, bismuth, antimony, copper, zinc, titanium, vanadium, chromium, molybdenum, manganese, iron, and cobalt are used. The catalysts can also be used without significant disadvantages in the form of their hydrates or ammoniates.

The following compounds are typical examples of such catalysts: lithium methanolate, lithium ethanolate, lithium propanolate, lithium butanolate, sodium methanolate, potassium tert-butanolate, magnesium methanolate, calcium methanolate, tin(II)chloride, tin(IV)chloride, lead acetate, lead phosphate, antimony(III)chloride, antimony(V)chloride, aluminum isobutylate, aluminum trichloride, bismuth(III)chloride, copper(II)acetate, copper(II)sulfate, copper(II)nitrate, bis(triphenylphospheneoxide)-copper-(II)-chloride, copper molybdate, silver acetate, gold acetate, zinc oxide, zinc chloride, zinc acetate, zinc acetonylacetate, zinc octoate, zinc oxalate, zinc hexylate, zinc benzoate, zinc undecylenate, cerium(IV)oxide, uranyl acetate, titanium tetrabutanolate, titanium tetrachloride, titanium tetraphenolate, titanium naphthenate, vanadium(III)chloride, vanadium acetonylacetate, chromium(III)chloride, molybdenum(IV)oxide, molybdenum acetylacetonate, tungsten(VI)oxide, manganese(II)chloride, manganese(II)acetate, manganese(III)acetate, iron(II)acetate, iron(III)acetate, iron phosphate, iron oxalate, iron(III)chloride, iron(III)bromide, cobalt acetate, cobalt chloride, cobalt sulfate, cobalt naphthenate, nickel chloride, nickel acetate, and nickel naphthenate as well as mixtures of such catalysts.

The catalysts are appropriately utilized in amounts from 0.0001 to 10 weight percent, preferably from 0.0001 to 3 weight percent, and more preferably, from 0.0005 to 1 weight percent, based on the weight of the allophanate and/or polyallophanate. In a special embodiment, the metal cations can also be present in the reaction mixture in a heterogeneous phase, for example, bound to ion exchangers.

The preparation of N,o-substituted mono- and/or polyurethanes in accordance with the process of the invention involves reacting the allophanates and/or polyallophanates with alcohols, preferably those corresponding to ester alcohols, in amounts per [—CO—NR$^1$—] group of from 1 to 5 moles, preferably from 3 to 15 moles, and more preferably from 3 to 5 moles.

If the ester alcohols R$^3$OH used as the basis of the allophanates and/or polyallophanates and the alcohols R$^2$OH, which are utilized, are identical, a transesterification occurs to a greater or lesser degree in addition to the alcoholysis. This results in polyurethanes and/or polyurethane mixtures with different ester groups. By suitably selecting the starting components, in particular the R$^2$OH alcohols, and the amounts of the starting components, however, nearly complete esterification can be achieved at the same time as the alcoholysis. This version of the process, alcoholysis with simultaneous transesterification, is particularly important when the mono- and/or polyurethanes are thermally cleaved into isocyanates and alcohols and the resulting cleavage products would have nearly the same boiling points without prior transesterification.

By reducing the amount of excess alcohol, the degree of transesterification can be reduced. However, it has proven to be desirable to perform the alcoholysis in the presence of solvents at [—CO—NR¹—] group-to-alcohol ratios of 1:1 to approximately 1:2.

The alcoholysis is performed at temperatures of at least 160° C., preferably from 165° to 250° C., and more preferably from 180° C. to 230° C. and at pressures of from 0.1 to 120 bar, preferably from 0.5 to 60 bar, and more preferably from 1 to 40 bar. At a given temperature, the reaction is then preferably performed under the intrinsic pressure of the reaction mixture.

For the temperature range cited, reaction times of from 0.5 to 100 hours result, preferably from 1 to 50 hours, and more preferably from 2 to 25 hours.

The mono- and/or polyurethanes are appropriately prepared in accordance with the process as follows. The allophanates and/or polyallophanates and R²OH alcohols are mixed in the cited quantitative ratios and, in some cases, in the presence of a catalyst and solvent, in a reaction vessel and heated, in some cases, while stirring. Then the mono- and/or polyurethanes are isolated from the resulting reaction mixture, in some cases after removal of the catalyst and filtering off of solids, for example by distilling off the excess alcohol, partially distilling off the excess alcohol, and removal through crystallization, by precipitating with other solvents or by recrystallization out of other solvents. If desired, the removed alcohol can be recycled.

In accordance with the process of the invention, as already described, mono- and/or polyurethanes can be prepared which have the formula $$R^1[-NHCOOR^2]_n,$$

where:

n is a whole number from 1 to 5, preferably 2 to 3, indicating the functionality, $R^1$, depending on the functionality of n, is a 1- to 5valent, preferably 2- to 3-valent, substituted or, preferably unsubstituted, aliphatic hydrocarbon radical having from 1 to 18, preferably 3 to 10, carbon atoms; substituted or, preferably unsubstituted, cycloaliphatic radical having from 3 to 18, preferably 6 to 13, carbon atoms; substituted or, preferably unsubstituted, aromatic hydrocarbon radical having from 6 to 15, preferably from 6 to 10, carbon atoms; a substituted or, preferably unsubstituted, aralaliphatic hydrocarbon radical having from 7 to 34 carbon atoms, preferably from 8 to 20 carbon atoms, or a substituted or, preferably unsubstituted, 5- to 6-member heterocyclic radical, which can also be connected to a benzene ring, and $R^2$ is a linear or branched alkyl radical having from 1 to 8, preferably 1 to 10, and more preferably 3 to 6, carbon atoms; a linear or branched alkyl radical having from 2 to 24, preferably 4 to 8, carbon atoms, substituted with alkoxy groups having from 1 to 4 carbon atoms or polyoxyalkylene groups, for example, polyoxyethylene and/or polyoxypropylene groups, or a substituted or unsubstituted cycloalkyl radical having from 4 to 12 carbon atoms, preferably from 6 to 8, and/or a substituted or unsubstituted arylaliphatic hydrocarbon radical having from 7 to 15 carbon atoms, preferably 7 to 10.

Typical substituents for the 1- to 5-valent aliphatic and cycloaliphatic radical $R^1$ are, for example: alkoxy groups having from 1 to 6, preferably 1 to 4, carbon atoms, aryoxy groups having from 6 to 10 carbon atoms, preferably 6 to 8, acyl radicals having from 2 to 6 carbon atoms, alkylmercapto groups having from 1 to 6 carbon atoms, arylmercapto groups having from 6 to 10 carbon atoms, alkylcarbonyl groups having from 1 to 10 carbon atoms, dialkylamino groups having from 1 to 10 carbon atoms, acylamino groups having from 1 to 8 carbon atoms, arylcarbonyl groups having from 7 to 9 carbon atoms, nitro groups, cyano groups, and halogen atoms.

The following 1- to 5-valent araliphatic and aromatic radicals $R^1$ can be mentioned as examples in addition to the substituents for the $R^1$ aliphatic and cycloaliphatic radicals cited above: linear or branched alkyl radicals having from 1 to 12, preferably from 1 to 4, carbon atoms, alkylsulfonates having from 1 to 10, preferably 1 to 4, carbon atoms in the linear or branched alkyl radical, and sulfonamide groups.

Preferred $R^1$ radicals are those which can be derived, for example, from the following primary amines: aliphatic and cycloaliphatic monoamines such as methylamine, ethylamine, propylamine, isopropylamine, n-butylamine, sec-butylamine, tert-butylamine, isobutylamine, 2- and 3-methylbutylamine, neopentylamine, n-pentylamine, 2-methylpentylamine, sec-isoamylamine, n-hexylamine, 2-methylhexylamine, 2-ethylhexylamine, n-heptylamine, n-octylamine, n-nonylamine, n-decylamine, n-dodecylamine, 2-phenylpropylamine, benzylamine, cyclopentylamine, cyclohexylamine, tert-butylcyclohexylamine, aliphatic diamines such as ethylenediamine, 1,3- and 1,2-propylenediamine, 2,2-dimethyl-1,3-propylenediamine, 2,2-dimethyl-1,3-propylenediamine, 1,4-butylenediamine, 1,5-pentamethylenediamine, 1,6-hexamethylenediamine, 2,2,4-trimethyl-1,6-hexamethylenediamine, 1,8-octamethylenediamine, 1,10-decylenediamine, 1,12-dodecylenediamine and 3,3'-diaminodipropyl ether, cycloaliphatic diamines such as 1,2-, 1,3-, and 1,4-cyclohexanediamine, 2,4- and 2,6-hexahydrotoluenediamine, as well as corresponding isomer mixtures, 1,4-hexahydroxylylenediamine, 4,4'-, 2,4'-, and 2,2'-diaminodicyclohexylmethane as well as corresponding isomer mixtures, 2,2-di(4-aminocyclohexyl)-propane, 3-aminomethyl-3,5,5-trimethylcyclohexylamine, and dicyclopentadienyl compounds of formula

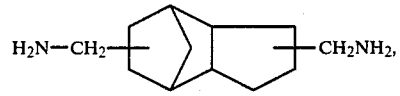

diamines containing heterocyclic radicals in bound form, such as, in some cases, substituted N,N'-bis-(aminoalkyl)piperazines, for example, N,N'-bis(2,2-dimethyl-3-aminopropyl)piperazine, and N,N'-bis-(aminopropyl)piperazine, aromatic monoamines such as aniline, substituted anilines, such as anilines substituted in the 2-, 3-, and/or 4-position by a nitro, methyl, ethyl, n-propyl, isopropyl, n-butyl, isobutyl, sec-butyl, tert-butyl group or by a chlorine atom, as well as similarly substituted ortho-, meta-, and/or para-hydroxy-, methoxy-, ethoxy-, propoxy-, isopropoxy-, N-butoxy-, isobutoxy-, sec-butoxy-, and tert-butoxyaniline; alkylbenzoates which are substituted by an amino group in the m- and/or p-position and contain from 1 to 12 carbon atoms in the alkyl radical, by N-alkoxycarbonylaminobenzenes and toluenes which are substituted by an amino group in the m- and/or p-position and which contain from 1 to 4 carbon atoms in the alkyl radical; α- and β-naphthylamine; aromatic diamines such as 1,3- and 1,4-diaminobenzene; 1,4-diaminobenzene, 1,5- and 1,8-diaminonaphthalene, 4,4'- diaminodiphenyl, 2,2'-, 2,4'-, and 4,4'-diaminodiphenylmethane substituted in the 2- and/or 4-position by a methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy group or a halogen atom, preferably a fluorine and/or a chlorine atom, and by the corresponding isomer mixtures as well as aromatic polyamines such as 1,3,5-triaminobenzene, 2,4,6-triaminotoluene, 1,3,5-triaminonaphthalene, and polyphenyl polymethylene polyamines as well as mixtures of diaminodiphenylmethanes and polyphenyl polymethylene polyamines.

Mono- and/or polyurethanes prepared in accordance with the process of the invention are valuable final products and intermediates. They are used as final products, for example, for pest control. As intermediates, they are used, for example, as components in condensation polymerization systems and polymer systems. In particular, though, they are transformed to the corresponding isocyanates by cleaving off alcohols, whereby di- and polyisocyanates are utilized to prepare polyurethane plastics.

The parts cited in the examples represent parts by weight. The elemental compositions and structures were determined by means of mass spectroscopy as well as IR and NMR spectra.

EXAMPLE 1

A mixture of 8.6 g N,N'-diphenylallophanic acid butyl ester and 15.9 g N-phenylbutylurethane was stirred with 58.1 g n-butanol for five hours at 210° C. After the reaction mixture had cooled, the excess n-butanol was distilled off, and 25.5 g N-phenylbutylurethane (90.2 percent of theoretical) was obtained after purification in a thin-film evaporator. The conversion of allophanate was quantitative.

A mixture of the starting components N,N'-diphenylallophanic acid butyl ester and N-phenylbutylurethane was obtained by stirring n-butanol with the distillation bottoms produced in the purification distillation of phenyl isocyanate, which, in turn, was produced by the thermal cleavage of N-phenylbutylurethane.

EXAMPLE 2

A mixture of 26 g of an allophanate obtained from 2-butoxycarbonylaminotoluene-4-isocyanate and 2,4-toluene dibutylurethane and 14 g 2,4-toluene dibutylurethane, obtained by stirring the distillation bottoms off the purification distillation of 2,4-toluene diisocyanate obtained through the thermal cleavage of 2,4-toluene dibutylurethane, was stirred for five hours at 210° C. with 51.8 g n-butanol. After cooling the reaction mixture, the excess n-butanol was distilled off, and a residue was obtained which contained 42.8 g, 2,4-toluene dibutylurethane, based on HPLC analysis, (98.0 percent of theoretical). Allophanate was not detected any longer.

EXAMPLE 3

In the purification distillation of a 1,6-hexamethylene diisocyanate obtained through the thermal cleavage of 1,6-hexamethylene dibutylurethane, 135 g of a mixture comprising 85 weight percent 6-(butoxycarbonylamino)hexylisocyanate and 15 weight percent 1,6-hexamethylene diisocyanate were heated at temperatures of 155° C. to 165° C. in the base of a distillation flask for an average of two hours. Here the result was a mixture comprising approximately 18 weight percent 6-(butoxycarbonylamino)hexylisocyanate and various polyisocyanato hexamethylene allophanic butyl esters.

An amount of 310 g n-butanol and 1 g iron(III)acetate were added to this mixture and the resulting mixture was then heated in a pressurized apparatus for five hours at 220° C. After cooling, the reaction mixture was analyzed using gas chromatography. An amount of 183 g 1,6-hexamethylene dibutylurethane was obtained. This meant that the polyisocyanato hexamethylene allophanic acid butyl esters were converted to diurethane at a nearly quantitative rate.

EXAMPLE 4

A procedure similar to that in Example 3 was followed, however, 78 g of a mixture comprising approximately 16 weight percent of 6-(butoxycarbonylamino)-hexylisocyanate, 450 g of n-octanol instead of n-butanol, and 0.5 g iron(III)acetate were used.

The reaction mixture was boiled for three hours, during which time the n-butanol cleaved off was removed by distillation, and after the reaction mixture had cooled, the excess n-octanol was distilled off at reduced pressure. The result was 153 g of a residue which thin-layer analysis revealed to consist of nearly quantitative amounts of 1,6-hexamethylene dioctylurethane.

The embodiments of the invention in which an exclusive privilege or property is claimed are defined as follows:

1. A process for the preparation of N,o-substituted mono- and/or polyurethanes of the formula

$$R^1[-NHCOOR^2]_n,$$

in which
  $R^1$ is an aromatic radical having from 6 to 15 carbon atoms which may be substituted,
  $R^2$ is selected from the group consisting of an alkyl radical having from 1 to 18 carbon atoms, a cycloalkyl radical having from 4 to 12 carbon atoms, an aralkyl radical having from 7 to 15 carbon atoms and an alkyl radical having from 2 to 24 carbon atoms substituted with alkoxy groups or polyoxyalkylene groups having from 1 to 4 carbon atoms, and n is a whole number from 1 to 5 wherein N-substituted allophanic acid and/or polyallophanate is reacted with alcohols in the presence or absence of catalysts at temperatures of at least 160° C.

2. The process of claim 1 wherein the reaction is performed at temperatures from 165° to 250° C.

3. The process of claim 1 wherein the reaction is performed in the presence of catalysts.

4. The process of claim 1 wherein from 0.0001 to 10 percent by weight of at least one cation of metals from groups IA, IB, IIA, IIB, IIIA, IIIB, IVA, IVB, VA, VB, VIB, VIIB, VIIIB in the periodic system based on the weight of the allophanic acid and/or polyallophanate is used as a catalyst.

5. The process of claim 1 wherein from 1 to 50 moles alcohol is used per —[CONR$^1$]— group in the allophanic acid and/or polyallophanate.

6. The process of claim 1 wherein the corresponding alcohol is used in the allophanic acid and/or polyallophanate.

7. The process of claim 1 wherein the alcohol is mixed with a solvent said solvent being inert at the reaction conditions.

8. The process of claim 1 wherein the alcohol is selected from the group consisting of linear or branched alkanols having from 1 to 18 carbon atoms, alkanols having from 2 to 24 carbon atoms substituted with alkoxy groups having from 1 to 4 carbon atoms or polyoxyalkylene groups, cycloaliphatic alcohols having from 4 to 12 carbon atoms, and/or araliphatic alcohols having from 7 to 15 carbon atoms.

9. The process of claim 1 wherein methanol, ethanol, n-propanol, iso-propanol, n-butanol, iso-butanol, n-pentanol, hexanol, ethylhexanol, heptanol, octanol, nonanol, decanol, cyclopentanol, benzyl alcohol, cyclohexanol and/or 2-phenylethanol are used as the alcohols.

* * * * *